United States Patent [19]

Bank

[11] Patent Number: 5,247,110
[45] Date of Patent: Sep. 21, 1993

[54] PHOSPHINOALIPHATICSILANE CATALYSTS FOR PREPARATION OF β-CYANOALKYLSILANES

[75] Inventor: Howard M. Bank, Freeland, Mich.

[73] Assignee: Dow Corning Corporation, Midland, Mich.

[21] Appl. No.: 998,708

[22] Filed: Dec. 30, 1992

[51] Int. Cl.$^5$ ............................................. C07F 7/10
[52] U.S. Cl. ............................................... 556/415
[58] Field of Search ................................... 556/415

[56] References Cited

U.S. PATENT DOCUMENTS

| | | | |
|---|---|---|---|
| 2,823,218 | 2/1958 | Sjeier | 556/415 |
| 2,860,153 | 11/1958 | Saam | 556/415 |
| 2,906,764 | 9/1959 | Jex et al. | 556/415 |
| 2,906,765 | 9/1959 | Jex et al. | 556/415 |
| 2,907,784 | 10/1959 | Jex et al. | 556/415 |
| 2,908,699 | 10/1959 | Jex et al. | 556/415 |
| 2,971,970 | 2/1961 | Bluestein | 556/415 |
| 3,257,440 | 6/1966 | Jex | 556/415 X |
| 4,614,812 | 9/1986 | Schilling | 556/415 X |
| 5,103,033 | 4/1992 | Bank | 556/415 |
| 5,126,468 | 6/1992 | Bank | 556/415 |
| 5,126,469 | 6/1992 | Bank | 556/415 |

OTHER PUBLICATIONS

Rajkumar et al Organometallics 8:549–550 (1989).
Czaková et al. J. of Molecular Catalysis 11:313–322 (1981).
Michalska et al. J. of Molecular Catalysis 11:323–330 (1981).

Primary Examiner—Paul F. Shaver
Attorney, Agent, or Firm—William F. Boley

[57] ABSTRACT

The present invention is a process for the preparation of β-cyanoalkylsilanes by contacting a mixture comprising trichlorosilane and an olefinic nitrile with novel phosphinoaliphaticsilane catalysts. The phosphinoaliphaticsilane catalysts are effective in the process as homogeneous catalysts or as supported heterogeneous catalysts. A preferred catalyst for the present process is a phosphinoaliphaticsilane on a solid support. The supported phosphinoaliphaticsilane catalysts have greater activity then the analogous homogeneous catalyst at lower temperatures.

38 Claims, No Drawings

PHOSPHINOALIPHATICSILANE CATALYSTS FOR PREPARATION OF β-CYANOALKYLSILANES

BACKGROUND OF INVENTION

The present invention is a process for the preparation of β-cyanoalkylsilanes by contacting a mixture comprising trichlorosilane and an olefinic nitrile with novel phosphinoaliphaticsilane catalysts. The phosphinoaliphaticsilane catalysts are effective in the process as homogeneous catalysts or as supported heterogeneous catalysts. A preferred catalyst for the present process is a phosphinoaliphaticsilane on a solid support. The supported phosphinoaliphaticsilane catalysts have greater activity than the analogous homogeneous catalyst at lower temperatures.

Beta-cyanoalkylsilanes having hydrolyzable chlorines bonded to the silicon atom are useful for the production of polyorganosiloxanes containing the β-cyanoalkyl substituent. The silicon-bonded β-cyanoalkyl substituent is extremely resistant to hydrolysis and cleavage under hot, humid conditions and impart these characteristics to the polyorganosiloxane of which they are a substituent. The presence of the silicon bonded β-cyanoalkyl substituent on polyorganosiloxanes also tends to stabilize the polyorganosiloxanes against swelling induced by liquid hydrocarbons. In addition, β-cyanoalkylsilanes having hydrolyzable chlorines are useful reactive intermediates for forming, for example, gamma-organoaminotrialkoxysilanes which are useful as surface treating agents.

It is known that when trichlorosilane is contacted with an olefinic nitrile, as exemplified by acrylonitrile, at a sufficient temperature a mixture of α-cyanoalkylsilanes and β-cyanoalkylsilanes is formed. In addition other reactions such as the formation of both silicon and non-silicon-containing complexes, homopolymerization of the starting nitrile, and the disproportionation of the starting silane can occur. The α-cyanoalkylsilanes are hydrolytically unstable. Therefore, the β-cyanoalkylsilanes generally have more commercial utility than the α-cyanoalkylsilanes and processes for producing high yields of β-cyanoalkylsilane are desirable.

A number of catalyst have been reported useful in the preparation of β-cyanoalkylsilanes. Saam, U.S. Pat. No. 2,860,153, issued Nov. 11, 1958, described a process for preparing β-cyanoethyltrichlorosilane by heating at a temperature less than 150° C. a mixture of acrylonitrile and trichlorosilane with a catalytic amount of an amine.

Jex et al., U.S. Pat. No. 2,906,764, issued Sep. 29, 1959, describes a process where organosilanes having at least one hydrogen and one hydrolyzable group bonded to silicon are reacted with an alkene nitrile in the presence of a diarylamine catalyst to produce preferentially β-cyanoalkylsilanes.

Jex et al., U.S. Pat. No. 2,907,784, issued Oct. 6, 1959, describes a process where organosilanes having at least one hydrogen and one hydrolyzable group bonded to silicon are reacted with an alkene nitrile in the presence of a trihydrocarbylphosphine catalyst to produce preferentially β-cyanoalkylsilanes.

Bluestein, U.S. Pat. No. 2,971,970, issued Feb. 14, 1961, describes a multiple component catalyst system useful for the production of β-cyanoalkylsilanes by the reaction of alkene nitriles with organosilanes having at least one hydrogen. The catalyst comprises a cuprous compound, a diamine, and a trialkylamine.

Rajkumar et al., Organometallics 8:549 (1989), describes a two-component catalyst effective in hydrosilation of acrylonitrile leading to the β-addition to the double bond of the acrylonitrile. The catalysts consist of cuprous oxide and tetramethylethylenediamine and is reported to be more effective that the previous catalysts taught by Bluestein, U.S. Pat. No. 2,971,970, issued Feb. 14, 1961. However, the present inventors have found that the process taught by Rajkumer et al. provides a crude mixture which can result in solid residues during subsequent distillation reactions to isolated the desired β-cyanoalkylsilanes. These solid reactants can clog the distillation apparatus making isolation of the desired β-cyanoalkylsilane difficult.

Czakova et al., J. of Molecular Catalysis 11:313 (1981), teaches that certain phosphinoaliphaticsilanes when complexed with rhodium are useful for the hydrogenation of alkenes. These phosphinoaliphaticsilanes complexed with rhodium were also found to be catalytic when supported on silica.

Michalska et al., J. of Molecular Catalysis 11:323 (1981) describes the reaction of hexene-1 with Me₂P-hSiH in the presence of a catalyst comprising a phosphinoaliphaticsilane and rhodium complex on silica.

The present invention is a high-yield process for the preparation of β-cyanoalkylsilanes. The process employs a single component catalyst comprising a phosphinoaliphaticsilane. It is not required that the phosphinoaliphaticsilane be complexed with a metal such as rhodium. No solid residues are generated during subsequent distillation steps to further isolate the β-cyanoalkylsilane. The process can be run as a homogeneous process or as a heterogeneous process where the phosphinoaliphaticsilane is on a solid support.

SUMMARY OF INVENTION

The present invention is a process for the preparation of β-cyanoalkylsilanes by contacting a mixture comprising trichlorosilane and an olefinic nitrile with novel phosphinoaliphaticsilane catalysts. The phosphinoaliphaticsilane catalysts are effective in the process as homogeneous catalysts or as supported heterogeneous catalysts. A preferred catalyst for the present process is a phosphinoaliphaticsilane on a solid support. The supported phosphinoaliphaticsilane catalysts have greater activity then the analogous homogeneous catalyst at lower temperatures.

DESCRIPTION OF INVENTION

The present invention is a process for the preparation of β-cyanoalkylsilanes described by formula

(1)

The process comprises: contacting a mixture comprising trichlorosilane and an olefinic nitrile described by formula

(2)

with an effective concentration of a catalyst comprising a phosphinoaliphaticsilane described by formula $$R_3SiR^2PR^3_2 \qquad (3)$$

at a temperature within a range of about 80° C. to 300° C.; where each R is independently selected from a group consisting of halogens, monovalent hydrocarbon radicals, substituted monovalent hydrocarbon radicals, alkoxy radicals, and aryloxy radicals; $R^2$ is an unsubstituted bivalent hydrocarbon radical comprising one to 20 carbon atoms; each $R^3$ is an independently selected monovalent hydrocarbon radical comprising one to 20 carbon atoms; and each Y is independently selected from a group consisting of hydrogen and alkyl radicals comprising one to eight carbon atoms.

In carrying out the process of the present invention, the olefinic nitrile, the trichlorosilane, and the phosphinoaliphaticsilane catalyst are contacted in a suitable reaction vessel. The type of reaction vessel is not critical to the present process. However, those skilled in the art will recognize that certain metal and metal complexes such as nickel halides can catalyze the formation of the alpha adducts of the olefinic nitrile. Also, the presence of certain metal compounds such as iron halides may poison the action of the phosphinoaliphaticsilane catalyst. Therefore, it is desirable to perform the process in reactors formed from non-reactive materials or to adjust the catalyst levels sufficient to mask the effects of contaminating metal and metal compounds.

The present process can be run as a batch, semi-continuous, or continuous process. The reactor can be, for example, a continuous-stir-tank reactor. When the phosphinoaliphaticsilane is supported, the reactor can be, for example, a packed-bed, a stirred-bed, a vibrating-bed, or a fluidized-bed type reactor. Preferred is a continuous process were the phosphinoaliphaticsilane is supported on a solid support.

A mixture comprising trichlorosilane and an olefinic nitrile described by formula (2) is contacted with a phosphinoaliphaticsilane catalyst described by formula (3). The mixture may be formed by feeding the olefinic nitrile and phosphinoaliphaticsilane catalyst separately to an appropriate reactor, or alternatively the mixture may be preformed and then fed to the reactor.

Contact of the mixture comprising trichlorosilane and an olefinic nitrile with the phosphinoaliphaticsilane catalyst can be effected by feeding the mixture to a reactor containing the phosphinoaliphaticsilane catalyst as either a homogeneous or heterogeneous catalyst. When the phosphinoaliphaticsilane is used in the process as a homogeneous catalyst, the phosphinoaliphaticsilane catalyst can be premixed with one or more of the components forming the mixture comprising the trichlorosilane and an olefinic nitrile and this mixture then fed to the heated reactor. The homogeneous phosphinoaliphaticsilane catalyst and the mixture comprising trichlorosilane and an olefinic nitrile can be fed separately to the reactor.

Olefinic nitriles useful in the present invention are described by formula (2), where each Y is independently selected from a group consisting of hydrogen and alkyl radicals comprising one to eight carbon atoms. The substituent Y can be, for example, hydrogen, methyl, ethyl, propyl, butyl, tert-butyl, and octyl. Preferred is when each substituent Y is independently selected from a group consisting of hydrogen and methyl. The olefinic nitrile can be, for example, acrylonitrile, methacrylonitrile, crotononitrile, ethylacrylonitrile, 1-cyanobutene-1, and 2-cyanooctene-1. Preferred is when the olefinic nitrile is acrylonitrile.

The trichlorosilane is provided to the reactor at a molar ratio within a range of about 0.9:1 to 100:1 in relation to the olefinic nitrile. Lessor molar ratios of trichlorosilane may be used but can result in reduced yields of the desired β-cyanoalkylsilane. Greater molar ratios of trichlorosilane may be used in the process, but may result in reduced process yields due to dilution of the olefinic nitrile. It is preferred that the molar ratio of trichlorosilane to olefinic nitrile be within a range of about 1:1 to 50:1.

Phosphinoaliphaticsilane catalysts useful in the present process are described by formula (3). In formula (3) each R is independently selected from a group consisting of halogens, monovalent hydrocarbon radicals, substituted monovalent hydrocarbon radicals, alkoxy radicals, and aryloxy radicals. Each R can be independently selected from a group consisting of, for example, chlorine, methyl, ethyl, propyl, isopropyl, butyl, tert-butyl, hexyl, cyclohexyl, phenyl, naphthal, xylyl, tolyl, 3,3,3-trifluoropropyl, perfluoropropyl, methoxy, ethoxy, propoxy, and phenoxy. Preferred is when R is selected from a group consisting of methoxy and ethoxy.

The phosphinoaliphaticsilane catalysts described by formula (3) contains substituent $R^2$, where $R^2$ is an unsubstituted bivalent hydrocarbon radical comprising one to 20 carbon atoms. Substituent $R^2$ can be, for example, an alkylene, cycloalkylene, arylene, or aralkylene. Preferred is when $R^2$ is selected from a group consisting of alkylenes comprising one to eight carbon atoms. Most preferred is when $R^2$ is selected from a group consisting of methylene and ethylene.

The phosphinoaliphaticsilane catalysts employed in the present process have two substituents $R^3$, where each $R^3$ is an independently selected monovalent hydrocarbon radical comprising one to 20 carbon atoms. The monovalent hydrocarbon radical $R^3$ can be, for example, methyl, ethyl, propyl, isopropyl, butyl, tert-butyl, hexyl, cyclohexyl, phenyl, naphthal, xylyl, tolyl. Preferred is when each $R^3$ is independently selected from a group consisting of monovalent hydrocarbon radicals comprising one to six carbon atoms. Most preferred is when each $R^3$ is phenyl.

The phosphinoaliphaticsilane catalysts can be used in the present process as a homogeneous catalyst or as a heterogeneous catalyst. By the term "homogeneous catalyst," it is meant that the phosphinoaliphaticsilane catalyst is not on a solid support. By the term "heterogeneous catalyst," it is meant that the phosphinoaliphaticsilane catalyst is provided to the process on a solid support.

The solid support material can be any material having siloxy substituents, i.e. SiOH, capable of reacting with one or more R—Si bonds of the phosphinoaliphaticsilane catalyst to effect retention of the phosphinoaliphaticsilane catalyst by the solid support material. The solid support material may be, for example, silicon metalloid, silica, silica gel, alumina, silica-alumina, or zeolites. The preferred solid support material is silica gel.

The solid support material can be in the form of, for example, flakes, chips, particles, powders, spheres, or tablets. Preferred is when the solid support material is less than about one centimeter in diameter. More preferred is when the solid support material is less than about 0.5 centimeter in diameter. The upper size limited of the solid support material is determined primarily by the surface area available to retain the phosphinoaliphaticsilane catalyst. Larger size diameters of solid support material may be used, but may result in an inability to provide optimal amounts of catalyst to the process. The lower size limit for the solid support material is determined by the practicalities of retaining, recovering, and handling of the material.

Binding of the phosphinoaliphaticsilane catalyst to the solid support can be effect by standard means, for example, as described in the present examples and as described in Czakova et al., J. of Molecular Catalysis, 11:313-322, 1981.

A useful concentration of the phosphinoaliphaticsilane retained by the solid support is where the phosphinoaliphaticsilane catalyst is about one to 30 weight percent of the weight of the solid support. Preferred is where the phosphinoaliphaticsilane catalyst is about five to 20 weight percent of the weight of the solid support.

In the present process, an effective concentration of a phosphinoaliphaticsilane catalyst is that which increases the rate of formation of the $\beta$-cyanoalkylsilane, improves the yield of $\beta$-cyanoalkylsilane, or both. A preferred effective concentration of the phosphinoaliphaticsilane catalyst is that which provides to the process a phosphorous concentration within a range of about $1 \times 10^{-6}$ to $5 \times 10^{-3}$ moles per milliliter of the mixture comprising the trichlorosilane and olefinic nitrile. A more preferred effective concentration of the phosphinoaliphaticsilane catalyst is that which provides to the process a phosphorous concentration within a range of about $1 \times 10^{-5}$ to $1 \times 10^{-4}$.

The process is conducted at a temperature within a range of about 50° C. to 300° C. When the process is conducted employing a homogeneous phosphinoaliphaticsilane catalyst, it is preferred that the process be conducted at a temperature within a range of about 130° C. to 200° C. When the process is conducted employing phosphinoaliphaticsilane on a solid support as catalyst, it is preferred that the process be conducted at a temperature within a range of about 100° C. to 170° C.

The present process is applicable for the preparation of $\beta$-cyanoalkylsilanes as exemplified by $\beta$-cyanoethyltrichlorosilane, $\beta$-cyano($\alpha$-methyl)ethyltrichlorosilane, $\beta$-cyano($\beta$-methyl)ethyltrichlorosilane, $\beta$-cyano($\alpha$-ethyl)ethyltrichlorosilane, and $\beta$-cyano($\beta$-ethyl)ethyltrichlorosilane.

The following examples are provided to illustrate the present invention. The examples are not intended to limited the scope of the present claims.

EXAMPLE 1

The ability of a catalyst comprising about six weight percent $(EtO)_3SiCH_2CH_2P(Ph)_2$ supported on silica gel to catalyze the reaction of trichlorosilane with acrylonitrile was evaluated.

To prepare the catalyst, 40.8 g of silica gel (Davison Chemical, Baltimore, Md.) was dried by azeotroping two hours under argon with 300 mL of toluene. Then 51 $\mu$L of the condensation agent n-hexylamine was added to the dried silica gel followed by 3.8 mL of $(EtO)_3SiCH_2CH_2P(Ph)_2$. The resultant mixture was refluxed for 2.5 hours with continuous stirring. The treated gel was then rinsed with dry toluene and then sufficient hexamethyldisilane was added to the reactor to cover the treated gel. This mixture was refluxed for two hours to silylate residual hydroxyls present on the treated gel. The treated gel was soxhlet extracted in hexane for 15.5 hours and then vacuum dried for two hours. The treated gel was analyzed for N, C, H, and P by standard analytical techniques and found to comprise by weight 0.18% N, 0.46% P, 6.14% C, and 1.05% H.

The catalyst's ability to catalyze the reaction of trichlorosilane with acrylonitrile was evaluated. The process was conducted in sealed 8 mm $\times$ 35 cm glass tubes, heat dried, and purged with argon. About 0.27 g of catalyst (0.04 mmole of phosphorous) was added to each tube. Then approximately 2.0 mL of a mixture comprising the trichlorosilane and the acrylonitrile in the proportions as described in Table 1 was added to each tube. The proportion of trichlorosilane to acrylonitrile is given as the mole percent excess of trichlorosilane added to the process in relation to the acrylonitrile. The tubes were heated for the times described in Table 1. After the tube was heated for the desired time it was removed from the oven and cooled in dry ice. The resultant product was warmed sufficiently to make it liquid and the liquid was analyzed by gas liquid chromotography (GLC) using a thermal conductivity (TC) detector. The results are presented in Table 1 as percent area under the readout curve (GLC-TC Area %) for each of the described compounds. In Table 1 the compound labelled "AN" is acrylonitrile and the level of tetrachlorosilane is provided as an indication of silane disproportionation in the process.

The catalyst used in Run 9a was recovered and reused as catalyst for runs 9b through 9e. Prior to each reuse the catalyst was washed with aliquots of trichlorosilane until the wash solution was clear. The catalyst was then washed with an aliquot of a mixture of the trichlorosilane and acrylonitrile in the proportions to be used in the subsequent run.

TABLE 1

Reaction of Trichlorosilane With Acrylonitrile Using Six Weight Percent $(EtO)_3 SiCH_2CH_2P(Ph)_2$ on Silica Gel as Catalyst

| Run No. | Mole % Excess $HSiCl_3$ | Temp. °C. | Length of Run(h) | GLC-TC Area % | | |
|---|---|---|---|---|---|---|
| | | | | AN | $SiCl_4$ | $Cl_3SiCH_2CH_2CN$ |
| 9a | 66 | 170–180 | 2.0 | 0.0 | 16.0 | 61.9 |
| 9b | 29 | 170–180 | 1.5 | 0.0 | 12.9 | 70.1 |
| 9c | 29 | 170–175 | 1.5 | 0.0 | 14.1 | 65.6 |
| 9d | 0 | 170–175 | 1.5 | 4.6 | 3.3 | 80.0 |
| 9e | 30 | 165–190 | 1.5 | 0.0 | 15.1 | 74.2 |

EXAMPLE 2

The ability of a catalyst comprising about nine to 12 weight percent $(EtO)_3SiCH_2CH_2P(Ph)_2$ supported on silica gel to catalyze the reaction of trichlorosilane with acrylonitrile was evaluated. The catalyst was evaluated both before and after treatment with hexamethyldisilizane to remove residual hydroxyls present on the silica gel.

To prepare the catalyst, 30.0 g of silica gel (Davison Chemical, Baltimore, Md.) was dried by azeotroping two hours under argon with 300 mL of toluene. Then 38 $\mu$L of the condensation agent n-hexylamine was added to the dried silica gel followed by about 8.9 mL of $(EtO)_3SiCH_2CH_2P(Ph)_2$. The resultant mixture was refluxed for 2.5 hours with continuous stirring. One portion of the treated gel (Untreated Cat.) was soxhlet extracted in hexane for six hours followed by vacuum drying for six hours. The untreated catalyst comprised about 12.3 weight percent $(EtO)_3SiCH_2CH_2P(Ph)_2$. A 15 g portion of the treated gel was further refluxed with 100 mL of hexamethyldisilizane for two hours (Treated Cat.) to silylate residual hydroxyls present on the treated gel. The treated catalyst was then soxhlet extracted and vacuum dried as described for the untreated catalyst. The treated catalyst comprised about 9.6 weight percent (EtO)$_3$SiCH$_2$CH$_2$P(Ph)$_2$. The dried untreated and treated catalyst were analyzed for N, C, H, and P by standard analytical techniques. The untreated catalyst was found to comprise by weight 0.0% N, 0.8% P, 6.3% C, and 1.0% H. The treated catalyst was found to comprise by weight 0.2% N, 0.7% P, 7.6% C, and 1.3% H.

Each Catalysts' ability to catalyze the reaction of trichlorosilane with acrylonitrile was evaluated by a process similar to that described in Example 1. The amount of catalyst employed in each run is reported in Table 2 as the millimole of phosphorous (mmole P) added to each tube. Approximately 2.0 mL of a mixture comprising the trichlorosilane and the acrylonitrile in the proportions as described in Table 2 (Mole % Excess HSiCl$_3$) was added to each tube. The tubes were heated for the times indicated in Table 2 and the contents recovered and analyzed as described in Example 1. The results are presented in Table 2 as percent area under the GLC-TC readout curve for each of the described compounds. In Table 2, the compound labelled "AN" is acrylonitrile and the level of tetrachlorosilane is provided as in indication of silane disproportionation.

TABLE 2

Reaction of Trichlorosilane With Acrylonitrile Using (EtO)$_3$SiCH$_2$CH$_2$P(Ph)$_2$ on Silica Gel as a Catalyst

| Type Cat. | Run Time(h) | Temp. °C. | mmole P | Mole % Excess HSiCl$_3$ | GLC-TC Area % | | |
|---|---|---|---|---|---|---|---|
| | | | | | AN | SiCl$_4$ | Cl$_3$SiCH$_2$CH$_2$CN |
| None | 1.5 | 111–122 | 0.00 | 51.9 | 34.7 | 1.2 | 0.0 |
| Untreated | 1.5 | 111–122 | 0.12 | 51.9 | 0.0 | 18.4 | 63.5 |
| Untreated | 0.5 | 165–180 | 0.14 | 16.0 | 4.0 | 20.5 | 58.4 |
| Untreated | 1.0 | 165–180 | 0.14 | 16.0 | 6.0 | 17.0 | 57.3 |
| Untreated | 1.5 | 165–180 | 0.14 | 16.0 | 3.3 | 21.8 | 60.2 |
| Treated | 1.5 | 111–122 | 0.08 | 51.9 | 4.8 | 13.3 | 58.4 |
| Treated | 0.5 | 165–180 | 0.12 | 16.0 | 1.9 | 14.8 | 68.7 |
| Treated | 1.0 | 165–180 | 0.10 | 16.0 | 1.4 | 15.3 | 72.2 |
| Treated | 1.5 | 165–180 | 0.11 | 16.0 | 0.0 | 14.4 | 76.7 |

EXAMPLE 3

The abilities of Ph$_3$P, (EtO)$_3$SiCH$_2$CH$_2$P(Ph)$_2$, and (EtO)$_3$SiCH$_2$CH$_2$P(Ph)$_2$ supported on silica gel to catalyze the reaction of trichlorosilane with acrylonitrile was evaluated. The process was run similar to that described for Example 1. Each of the tested catalyst was added to the process sufficient to provide 8.3×10$^{-5}$ moles of phosphorous per 2.0 mL of a mixture comprising 10 mole percent excess trichlorosilane in relation to the acrylonitrile. The Ph$_3$P (Aldrich, Milwaukee, Wis.) was tested for comparison purposes only and is not within the scope of the present claims. The (EtO)$_3$SiCH$_2$CH$_2$P(Ph)$_2$ was acquired from Huls, Piscataway, N.J.

The (EtO)$_3$SiCH$_2$CH$_2$P(Ph)$_2$ supported on silica gel (Supported Cat.) was prepared the same as the treated catalyst described in Example 2.

The activity of each of the three catalysts for catalyzing the reaction of trichlorosilane with acrylonitrile was evaluated at 120° C. for two hours and at 170° C. for two hours. The resultant products were analyzed by as GLC-TC and the results are presented in Table 3. The type catalyst (Type Cat.), temperature at which the process was conducted (Temp. °C.), the area percent of Cl$_3$SiCH$_2$CH$_2$CN under the GLC-TC trace (GLC-TC Area %, Cl$_3$SiCH$_2$CH$_2$CN), and the ratio of the GLC-TC area percent of Cl$_3$SiCH$_2$CH$_2$CN to GLC-TC area percent of the SiCl$_4$ formed in the process (SiCl$_4$ Ratio) are provided in Table 3 under the appropriately labelled headings. The SiCl$_4$ Ratio is provided as an indication of the potential for disproportionation of trichlorosilane in the process.

TABLE 3

Comparison of Ability of Unsupported and Supported (EtO)$_3$SiCH$_2$CH$_2$CN to Catalyze the Reaction of Trichlorosilane With Acrylonitrile.

| Type Cat. | Temp.°C. | GLC-TC Area % (EtO)$_3$SiCH$_2$CH$_2$CN | SiCl$_4$ Ratio |
|---|---|---|---|
| Ph$_3$P | 120 | 4.7 | 0.5 |
| Ph$_3$P | 170 | 70.2 | 6.8 |
| (EtO)$_3$SiCH$_2$CH$_2$CN | 120 | 29.6 | 2.6 |
| (EtO)$_3$SiCH$_2$CH$_2$CN | 170 | 73.3 | 4.7 |
| Supported Cat. | 120 | 63.6 | 4.6 |
| Supported Cat. | 170 | 67.9 | 3.8 |

The results demonstrate that all three catalyst perform similarly at 170° C. However, at 120° C. (EtO)$_3$SiCH$_2$CH$_2$CN supported on silica gel demonstrates greater activity than the other two catalysts tested.

I claim:

1. A process for preparation of β-cyanoalkylsilanes described by formula

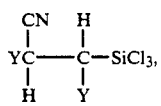

the process comprising: contacting a mixture comprising trichlorosilane and an olefinic nitrile described by formula

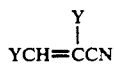

with an effective concentration of a phosphinoaliphaticsilane catalyst described by formula

at a temperature within a range of about 80° C. to 300° C.; where each R is independently selected from a group consisting of halogens, monovalent hydrocarbon radicals, substituted monovalent hydrocarbon radicals, alkoxy radicals, and aryloxy radicals; R$^2$ is an unsubstituted bivalent hydrocarbon radical comprising one to 20 carbon atoms; each R$^3$ is an independently selected monovalent hydrocarbon radical comprising one to 20 carbon atoms; and each Y is independently selected from a group consisting of hydrogen and alkyl radicals comprising one to eight carbon atoms.

2. A process according to claim 1, where the phosphinoaliphaticsilane catalyst is a homogeneous catalyst.

3. A process according to claim 2, where each substituent Y is independently selected from a group consisting of hydrogen and methyl.

4. A process according to claim 2, where the olefinic nitrile is selected from a group consisting of acrylonitrile, methacrylonitrile, crotononitrile, ethylacrylonitrile, 1-cyanobutene-1, and 2-cyanooctene-1.

5. A process according to claim 2, where the olefinic nitrile is acrylonitrile.

6. A process according to claim 2, where the trichlorosilane is provided to the process at a molar ratio within a range of about 0.9:1 to 100:1 in relation to the olefinic nitrile.

7. A process according to claim 2, where the trichlorosilane is provided to the process at a molar ratio within a range of about 1:1 to 50:1 in relation to the olefinic nitrile.

8. A process according to claim 2, where each R is independently selected from a group consisting of methoxy and ethoxy.

9. A process according to claim 2, where $R^2$ is selected from a group consisting of alkylenes comprising one to eight carbon atoms.

10. A process according to claim 2, where $R^2$ is selected from a group consisting of methylene and ethylene.

11. A process according to claim 2, where each $R^3$ is independently selected from a group consisting of monovalent hydrocarbon radicals comprising one to six carbon atoms.

12. A process according to claim 2, where $R^3$ is phenyl.

13. A process according to claim 2, where the effective concentration of the phosphinoaliphaticsilane catalyst is that which provides to the process a phosphorous concentration within a range of about $1 \times 10^{-6}$ to $5 \times 10^{-3}$ moles per milliliter of the mixture comprising the trichlorosilane and olefinic nitrile.

14. A process according to claim 2, where the effective concentration of the phosphinoaliphaticsilane catalyst is that which provides to the process a phosphorous concentration within a range of about $1 \times 10^{-5}$ to $5 \times 10^{-4}$ moles per milliliter of the mixture comprising the trichlorosilane and olefinic nitrile.

15. A process according to claim 2, where the temperature is within a range of about 130° C. to 200° C.

16. A process according to claim 2, where the β-cyanoalkylsilane is selected from a group consisting of β-cyanoethyltrichlorosilane, β-cyano(α-methyl)ethyltrichlorosilane, β-cyano(β-methyl)ethyltrichlorosilane, β-cyano(α-ethyl)ethyltrichlorosilane, and β-cyano(β-ethyl)ethyltrichlorosilane.

17. A process according to claim 1, where the phosphinoaliphaticsilane catalyst is a homogeneous, catalyst, each R is independently selected from a group consisting of methoxy and ethoxy, $R^2$ is selected from a group consisting of methylene and ethylene, $R^3$ is phenyl, the effective concentration of the phosphinoaliphaticsilane catalyst is that which provides to the process a phosphorous concentration within a range of about $1 \times 10^{-5}$ to $5 \times 10^{-4}$ moles per milliliter of the mixture comprising the trichlorosilane and olefinic nitrile, the olefinic nitrile is selected from a group consisting of acrylonitrile and methacrylonitrile, the trichlorosilane is provided to the process at a molar ratio within a range of about 1:1 to 50:1 in relation to the olefinic nitrile, and the temperature is within a range of about 130° C. to 200° C.

18. A process according to claim 1, where the phosphinoaliphaticsilane catalyst is supported on a solid support material.

19. A process according to claim 18, where the process is a continuous process.

20. A process according to claim 18, where each substituent Y is independently selected from a group consisting of hydrogen and methyl.

21. A process according to claim 18, where the olefinic nitrile is selected from a group consisting of acrylonitrile, methacrylonitrile, crotononitrile, ethylacrylonitrile, 1-cyanobutene-1, and 2-cyanooctene-1.

22. A process according to claim 18, where the olefinic nitrile is acrylonitrile.

23. A process according to claim 18, where the trichlorosilane is provided to the process at a molar ratio within a range of about 0.9:1 to 100:1 in relation to the olefinic nitrile.

24. A process according to claim 18, where the trichlorosilane is provided to the process at a molar ratio within a range of about 1:1 to 50:1 in relation to the olefinic nitrile.

25. A process according to claim 18, where each R is independently selected from a group consisting of methoxy and ethoxy.

26. A process according to claim 18, where $R^2$ is selected from a group consisting of alkylenes comprising one to eight carbon atoms.

27. A process according to claim 18, where $R^2$ is selected from a group consisting of methylene and ethylene.

28. A process according to claim 18, where each $R^3$ is independently selected from a group consisting of monovalent hydrocarbon radicals comprising one to six carbon atoms.

29. A process according to claim 18, where $R^3$ is phenyl.

30. A process according to claim 18, where the solid support material is selected from a group consisting of silicon metalloid, silica, silica gel, alumina, silica-alumina, and zeolite.

31. A process according to claim 18, where the solid support material is silica gel.

32. A process according to claim 18, where the phosphinoaliphaticsilane catalyst is about one to 30 weight percent of the weight of the solid support material.

33. A process according to claim 18, where the phosphinoaliphaticsilane catalyst is about five to 20 weight percent of the weight of the solid support material.

34. A process according to claim 18, where the effective concentration of the phosphinoaliphaticsilane catalyst is that which provides to the process a phosphorous concentration within a range of about $1 \times 10^{-5}$ to $5 \times 10^{-3}$ moles per milliliter of the mixture comprising the trichlorosilane and olefinic nitrile.

35. A process according to claim 18, where the effective concentration of the phosphinoaliphaticsilane catalyst is that which provides to the process a phosphorous concentration within a range of about $1 \times 10^{-5}$ to $5 \times 10^{-4}$ moles per milliliter of the mixture comprising the trichlorosilane and olefinic nitrile.

36. A process according to claim 18, where the temperature is within a range of about 100° C. to 170° C.

37. A process according to claim 18, where the β-cyanoalkylsilane is selected from a group consisting of β-cyanoethyltrichlorosilane, β-cyano(α-methyl)ethyltrichlorosilane, β-cyano(β-methyl)ethyltrichlorosilane, β-cyano(α-ethyl)ethyltrichlorosilane, and β-cyano(β-ethyl)ethyltrichlorosilane.

38. A process according to claim 1, where the phosphinoaliphaticsilane catalyst is supported on silica gel, the phosphinoaliphaticsilane catalyst is about five to 20 weight percent of the weight of the silica gel, the effective concentration of the phosphinoaliphaticsilane catalyst is that which provides to the process a phosphorous concentration within a range of about $1 \times 10^{-5}$ to $5 \times 10^{-4}$ moles per milliliter of the mixture comprising the trichlorosilane and olefinic nitrile, each R is independently selected from a group consisting of methoxy and ethoxy, $R^2$ is selected from a group consisting of methylene and ethylene, $R^3$ is phenyl, the olefinic nitrile is selected from a group consisting of acrylonitrile and methacrylonitrile, the trichlorosilane is provided to the process at a molar ratio within a range of about 1:1 to 50:1 in relation to the olefinic nitrile, and the temperature is within a range of about 100° C. to 170° C.

* * * * *